United States Patent [19]

Brinckmann et al.

[11] Patent Number: 4,687,486
[45] Date of Patent: Aug. 18, 1987

[54] IMPLANT, PARTICULARLY ENDOPROSTHESIS

[75] Inventors: Paul Brinckmann, Münster; Emmanuel Anapliotis, Berlin, both of Fed. Rep. of Germany

[73] Assignee: MECRON medizinische Produkte GmbH, Berlin, Fed. Rep. of Germany

[21] Appl. No.: 586,555

[22] Filed: Mar. 5, 1984

[30] Foreign Application Priority Data

Mar. 4, 1983 [DE] Fed. Rep. of Germany ....... 3308229
May 30, 1983 [DE] Fed. Rep. of Germany ....... 3319916

[51] Int. Cl.$^4$ ............................................. A61F 2/30
[52] U.S. Cl. ........................................ 623/16; 623/18; 623/23
[58] Field of Search ......................... 3/1.9, 1.91, 1.911, 3/1.912, 1.913; 128/92 C, 92 CA; 623/11, 16, 18, 19, 20, 21, 22, 23

[56] References Cited

U.S. PATENT DOCUMENTS

| | | | |
|---|---|---|---|
| 1,470,313 | 10/1923 | Woolen | 128/92 E |
| 2,014,638 | 9/1935 | Scofield | 128/92 E |
| 3,864,758 | 2/1975 | Yakich | 128/92 CA |
| 4,012,795 | 3/1977 | Dorre et al. | 128/92 CA |
| 4,187,841 | 2/1980 | Knutson | 128/92 E |
| 4,384,373 | 5/1983 | Sirash | 623/18 |
| 4,404,691 | 9/1983 | Bunning et al. | 128/92 C |
| 4,467,794 | 8/1984 | Maffei et al. | 128/92 YZ |
| 4,553,273 | 11/1985 | Wu | 623/18 |

Primary Examiner—Richard J. Apley
Assistant Examiner—David J. Isabella
Attorney, Agent, or Firm—Spencer & Frank

[57] ABSTRACT

Implant composed of a first part having a receptacle; a second part having a pin projecting therefrom, the pin having a conical portion located at the free end of the pin and tapering toward the free end of the pin, the conical portion being insertable into the receptacle to connect the parts together, the pin further having a threaded portion axially spaced from the conical portion; and a nut threadedly engaging the threaded portion for movement toward the first part in a manner to force the first and second parts apart.

18 Claims, 7 Drawing Figures

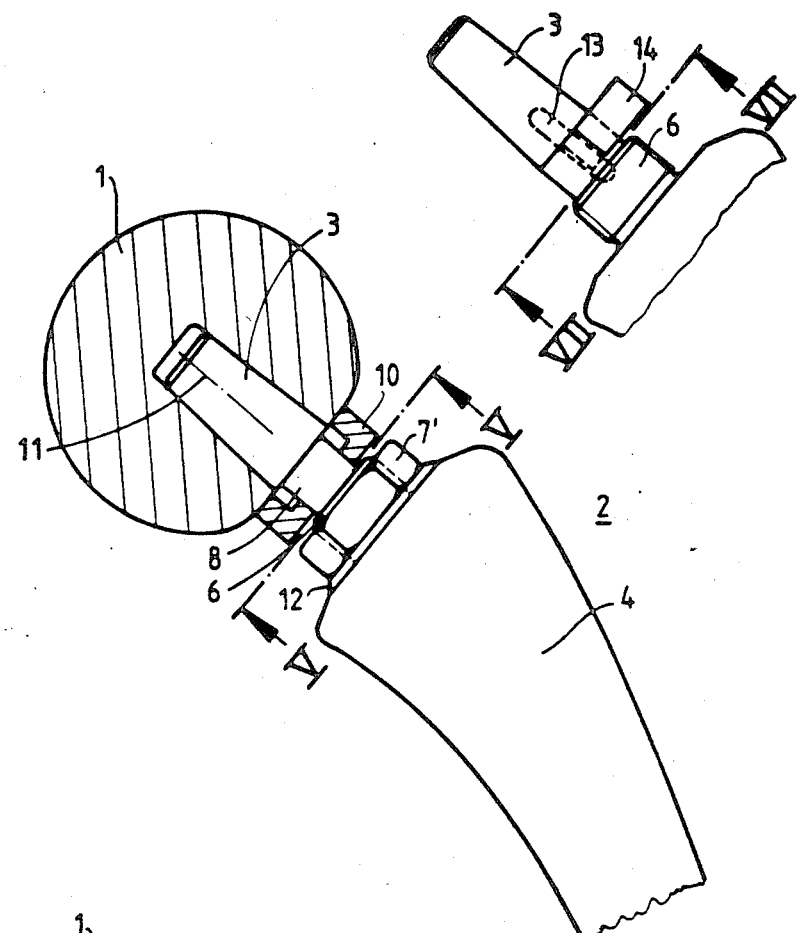
Fig. 6
Fig. 4
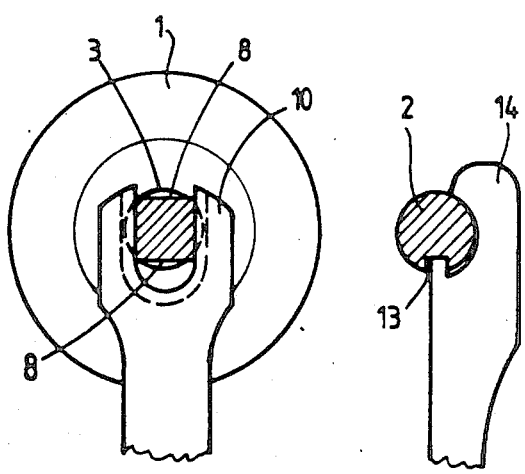
Fig. 5   Fig. 7

IMPLANT, PARTICULARLY ENDOPROSTHESIS

BACKGROUND OF THE INVENTION

The present invention relates to an implant, particularly an endoprosthesis, composed of a first part which can be plugged onto a conical pin provided at a second part.

For implants, particularly endoprostheses, the necessity may arise to replace or re-anchor part, of the implant In order to avoid, when replacing one part, the explantation of the other part of the implant, which is firmly cemented into the bone, the first part must be separated, for the replacement, from the second part which remains in the bone. This separation of parts wedged in one another requires large forces and there exists the danger of damage to bone or tissue due to manipulation accidents, for example slippage of the chisel-like tool usually used for effecting the separation.

Such implants are used with preference as prostheses for hip or knee joints. In such cases, the second part includes, in addition to a shaft, a conical pin onto which the first part including the artificial joint surface is placed. This surface is subject to wear which may also result in the respective part of the prosthesis having to be replaced. Moreover, even if only the other associated joint surface has to be exchanged during renewed surgery, it is advisable to replace the second part together with the joint surface since this requires only slightly greater expenditures and will possibly save the expense of a subsequent operation. Thus both joint surfaces are replaced in one operation. Then the operating surgeon no longer needs to make efforts to avoid damaging the joint surfaces by any means at the proposed implant.

SUMMARY OF THE INVENTION

The present invention has as an object to provide an implant of the above-described type in which the two prosthesis parts can be easily separated from one another, and particularly without impairing the strength and durability of the plug-in connection between the two parts.

The present invention is based on the realization that loosening of prosthesis parts which are connected together in a manner that is stable under loads is possible in a particularly favorable manner by provision of an element which is an integral component of the implant and is fastened in the bone together therewith.

The above and other objects are achieved, according to the invention, by the provision of an implant composed of a first part having a receptacle; a second part having a pin projecting therefrom, the pin having a conical portion located at the free end of the pin and tapering toward the free end of the pin, the conical portion being insertable into the receptacle to connect the parts together, the pin further having a threaded portion axially spaced from the conical portion; and a nut threadedly engaging the threaded portion for movement toward the first part in a manner to force the first and second parts apart.

When two prosthesis parts equipped with the present invention are joined together, the nut is slipped over the cone before the connection is made and is screwed onto the thread until it reaches an abutment or other limitation before both parts are firmly plugged together with the aid of the conical pin. For the later release of this plug-in connection, the nut is screwed back so that the first part, which has been plugged onto the conical pin, is lifted off the cone.

When the nut is screwed back, the second part must be held fast. It is therefore advisable to provide work surfaces at which a holding tool can engage so as to tranfer a torque which prevents rotation about the thread axis.

According to particular embodiments of the invention, the nut is provided with circumferential teeth, grooves or holes such that a tool corresponding in function to a nut key is able to engage at a pin, tongue or countertooth in a corresponding recess in the nut and permits loosening or tightening by means of short angular strokes. This permits manipulation by means of a simple tool, with the point of engagement of the pin or countertooth of the tool preferably being disposed at the side facing away from the operator so that the force holding the pin in engagement can be compensated by the influence of the holding tool in the form of a wrench and thus likewise prevents the generation of forces which might loosen the firm seat of the implanted shaft. If the holding tool employed is a slotted key, the tongue must be attached, for this reason, opposite the corresponding tongue of the other key—when seen with respect to identically oriented keys—so that the forces holding the tongues in engagement are compensated.

If in the range of engagement of the key, the circumference of the nut is made larger—in order to accommodate the corresponding recesses and to reduce the forces to be transmitted in the recess when a torque is applied to loosen the nut—and is reduced to the cross-section of the axial forces generated to transfer them to the joint ball, this simultaneously results in the advantage that the mobility of the joint socket compared to a cone end without nut is hardly restricted. The work faces for the tool holding the other part are here preferably applied in the form of chamfers at the prosthesis shaft since gripping the joint ball is difficult and requires at least a set of tools adapted to the respective ball size.

According to a preferred embodiment, the present invention is used in an implant to bridge large resections in the region of joints. Such an implant takes over the function of an extremity, particularly a leg, if in the region of the joint (hip or knee joint) up to one third of the proximal or distal components of the femur and/or proximal components of the tibia have been cut out. Such resections may become necessary in connection with primary bone tumors, skeletal metastases or after repeated artificial knee replacements as a result of infections. The shaft portions equipped with conical ends or cone receiving ends of different lengths can here be connected together and—with the measures according to the present invention—released again without particular difficulties.

In a favorable embodiment of a knee joint replacement, the implant is not made in the form of a joint; it is to be implanted where the lack of muscular prerequisites does not permit the use of a further artificial knee joint replacement. Here again the preferred embodiment is a modular set of implants, comprising a set of implants graduated in size, for implantation in the shaft of the tibia. Femur implants are provided with an internal cone at one end; tibia implants have an external cone.

During manufacture of the implant sets, their dimensions are selected preferably uniformly so that each implant part of any length can be combined with any other implant part of any length. The plug-in cone assures the rotationally stable connection of the parts once they have been plugged together and subjected to a load just once. The respective part carrying the external cone is provided with a nut which moves on a thread below the external cone and which can be used to release the conical plug-in connection in case the implant must be removed again.

Particularly for "collarless" hip joint prostheses, wherein the pin of the second part merges without transition into the shaft, it has been found that the proposed implant cannot be used too well. In particular, it is difficult to prevent rotation about the thread axis between the shaft and the screwed-on nut with which the first part, i.e. the artificial joint ball, can be lifted from the conical portion of the second part. It has also been found to be difficult to hold the first part during rotation of the nut; due to the different ball diameters, different tools would have to be made available, which moreover are rather cumbersome to manipulate, particularly if the ball diameters are large. Moreover, the tools have a poor grip at the smooth ball surface so that the danger always exists that the poor seat of the tool promotes the formation of chips which drop into the wound and could lead to complications. It has further been found that in the proposed implant the nut may impair the mobility of the artificial joint.

The present invention now makes it possible that the first part can always be released from the second part with the aid of a nut disposed on the second part between shaft and cone. If it is undesirable to apply chamfers for engagement of a tool at implant parts, particularly in connection with "collarless" hip joint prostheses where the pin of the second part merges into the shaft without defined edges, according to an advantageous feature of the invention, a space is provided between the cone end and the shaft and between the nut and the first part (e.g. the joint ball). In this space, work faces for a holding tool are provided at the first part so that twisting of the implant during rotation of the nut can be prevented and no forces are generated to impair the firm seat of the implanted prosthesis shaft.

Thus, in order to release the first part from the second part of the implant, the holding tool is applied in the region of the work faces, the nut is rotated in the direction toward the holding tool and thus the holding tool is pressed against the first part. During further rotation of the nut, the holding tool is shifted on the work faces at the first part of the implant. The holding tool here serves as a spacer between the nut and the first part. It transfers the forces from the nut to the first part since the first part is lifted off in this way from the cone of the second part.

Since in the implanted state a space now exists between the first part and the nut where the work faces are, it is possible to provide greater mobility for an adjacent joint, which is comprised, for example, of the joint head and an artificial hip socket.

BRIEF DESCRIPTION OF THE DRAWING

FIG. 4 is a view similar to that of FIG. 1, of a further embodiment of a combination of parts in the form of a hip joint prosthesis with an associated holding tool.

FIG. 5 is a cross-sectional view along line V—V of FIG. 4.

FIG. 6 is an elevational detail view of a modified version of the embodiment of FIG. 4.

FIG. 7 is a cross-sectional view along line VII—VII of FIG. 6.

DESCRIPTION OF THE PREFERRED EMBODIMENTS

Figure 1:
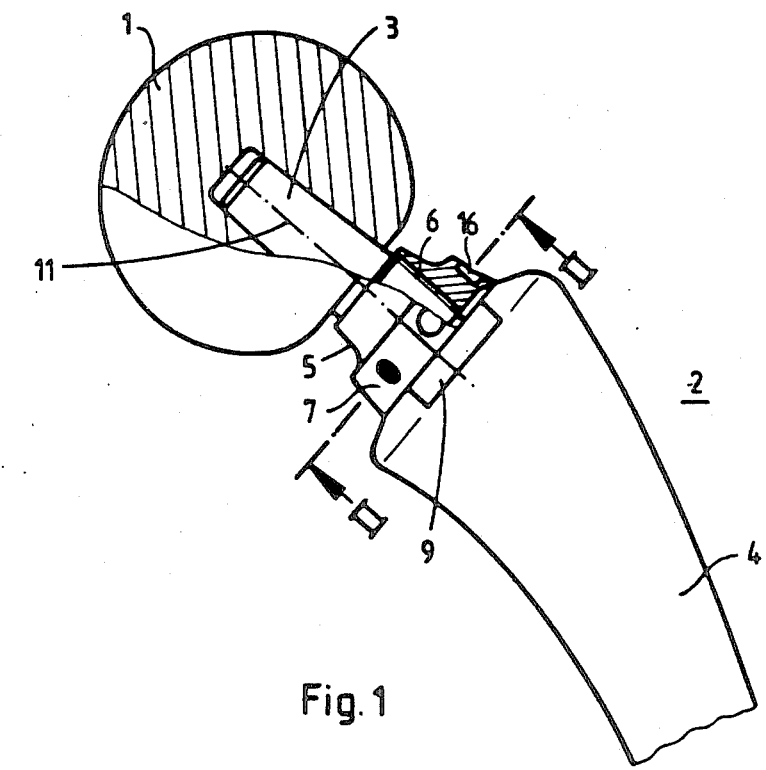
FIG. 1 is an elevational view, partly in cross-section, of a first advantageous embodiment in the form of a hip joint prosthesis.

FIG. 1 is a schematic representation of the head region of an artificial hip joint prosthesis according to the invention having a first part 1 constituting a ball joint. The right-hand portion of the head region is here shown in cross-section. This first part 1 is plugged onto a conical pin 3 of the second part 2 which also includes a shaft 4. Between the base of pin 3 and its conical free end, pin 3 is provided with a thread 6 onto which a nut 7 is screwed. In the illustrated state, i.e. in the implanted state of the prosthesis, this nut is located at a possibly slight distance from the first part 1 of the prosthesis.

If now this first part 1 is to be released from the second part 2, nut 7 is screwed in the direction toward the free end of pin 3 until the first part 1 is pushed loose from pin 3.

During rotation of nut 7, the second part 2 must be held back from rotation. For this purpose, part 2 is provided with work faces 9 in the form of symmetrical lateral chamfers, or flats, via which part 2 can be gripped by a holding tool, for example, a wrench, with the aid of which rotation of the shaft 4 about the thread axis can be prevented. In the illustrated position, the oppositely disposed chamfer is disposed to the rear of the drawing plane and is not visible.

Only relatively slight forces are required to release the two parts 1 and 2 from one another because thread 6, cooperates with nut 7, in the manner of a worm gear, providing strong force transfer with respect to the torques acting on the nut for the axial forces required to release the parts from one another.

Figure 2:
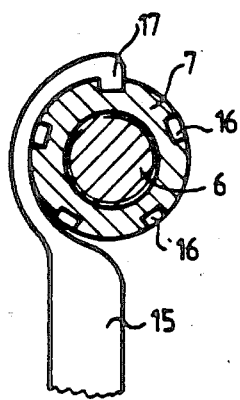
FIG. 2 is a cross-sectional view along the line II—II of FIG. 1 with the associated actuation tool.

FIG. 2 is a cross-sectional end view of nut 7 with the associated actuating tool 15. Nut 7 has an essentially cylindrical or conical jacket shaped outer contour in which hole-type recesses 16 are uniformly distributed in the circumferential direction. Tool 15 has a tongue 17 designed as a countertooth engageable into these recesses 16 so that tightening or releasing of nut 7' is possible by short angular strokes of tool 15 if engagement occurs in respectively successive recesses 16. Tongue 17 is adapted in shape to the shape of recesses 16—i.e. if each recess has the shape of a blind bore, tongue 17 has the shape of a cylindrical pin. Recesses 16 may be distributed over the circumferential direction at larger or smaller intervals, as required. Correspondingly, the recesses may also have polygonal cross-sections.

The point of engagement of the countertooth, tongue, or pin 17 is disposed at the side of the shaft facing away from the operator of tool 15 so that the forces generated during tightening or loosening of nut 7' are substantially compensated when a wrench is used to clamp onto faces 9 to counteract these forces since the wrench requires a compressive or pushing force to be applied for the counteraction, while the engagement of the countertooth or pin 17 requires a pulling force component. In differently configured holding tools, force compensation is provided by arranging the tongues which engage in the shaft so as to be opposite one another during use.

By giving nut 7 a cylindrical or cone jacket shaped outer surface with recesses 16 therein, a shape can be realized which, with respect to its outer contour—except for the recesses 16—is substantially adapted to that of the transition region between prosthesis shaft 4 and cone 3.

Preferably, the region 5 of nut 7 adjacent cone 3, in an endoprosthesis including a ball joint 1 of the type shown in FIG. 1, is made as slender as possible so that the range of mobility of the associated joint socket (not shown in the drawing) is not much restricted. Recesses 16 are disposed at the axial end of nut 7 which is remote from joint ball 1. This also assures optimum transition of contours to shaft 4, with the length of the nut likewise being adapted to various neck lengths.

Figure 3:
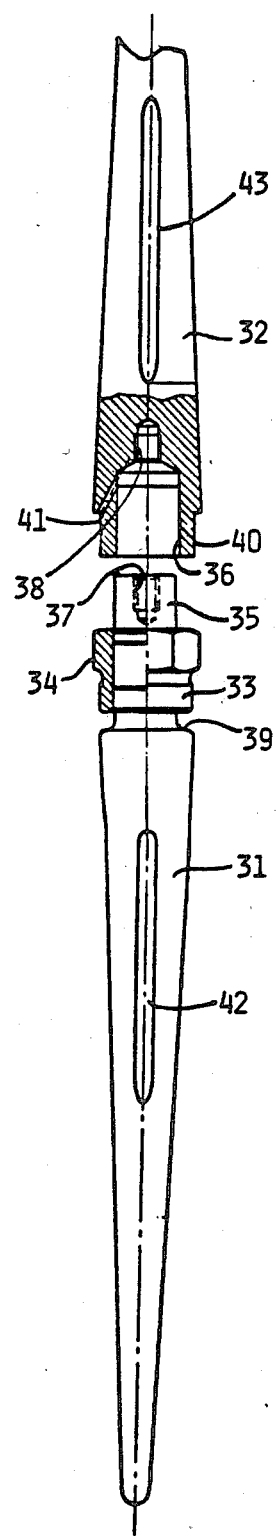
FIG. 3 is an elevational view, partly in cross-section, of an embodiment of the invention in the form of an implant to bridge bone defects in the region of the knee joint.

FIG. 3 shows an implant for bridging larger bone defects in the region of the knee joint. It comprises a first part 31 for anchoring in the tibia and a second part 32 for anchoring in the femur. The function and arrangement of a nut 34 screwed to a threaded portion of a cone 35 corresponds to the embodiment shown in FIG. 1. The thread extends a sufficient distance to allow nut 34 to be screwed on beyond the part of cone 35 which is to engage in a mating recess 36 in part 32.

Both parts are additionally provided with threaded blind bores 37 and 38, respectively, which may serve to accommodate a tool for holding or pulling out the respective part.

The arrangement illustrated in FIG. 3 shows the two implant parts in their position shortly after release, with nut 33 being shown in a position at a slight distance from an abutment 39 of part 31, against which abutment it is screwed when the arrangement is in the implanted state. To serve as a counterhold during rotation of nut 34 to separate the parts, chamfers, or flat surfaces, 40 and 41 are provided in femur portion 32. This arrangement is actually surprising since, according to mechanical laws, holding should actually occur at part 31 and a countermoment should be produced. However, since part 31 is accessible only with difficulty, the counterhold may be correspondingly effected at the femur part 32 until the connection is released—and that is why force is required.

Nut 34 has the form of a conventional nut having a polygonal periphery and is provided with a reduced diameter portion 33 at one end.

The implantation of the implant according to the present invention is advisably effected as follows:

The implants are selected from a supply depending on the height of the resection made at the femur and at the tibia. Selection is here made according to the condition that the implants must still be anchorable securely in the bone and the length of the leg must be adapted as well as possible to the length of the healthy leg. Anchoring in the bone is effected by means of bone cement, analogously to the procedures for artifical joint replacements. The implants have a smooth, conical shape; however, they are each provided with an additional groove 42 and 43, respectively which has been cut in in the longitudinal direction to secure rotation stability in the cement base. Cement free implantation is also possible. The surface would then have to be made different, i.e. it would have to be structured to the bone recess.

The implantation instruments include a set of sample parts which simplify selection from the modular system, two keys which permit releasing of a plugged together cone and a hook for pulling out the implants (for this purpose, the implants and the sample parts are provided with the above-mentioned internally threaded bores 37 and 38).

Any implantable metal alloy can be used as the material for the implants; for reasons of weight, a titanium alloy, such as, for example TiAlV64 is favorable.

FIG. 4 is a schematic representation of a hip joint head, including a first part 1 including a joint ball shown in cross-section. This first part 1 is placed onto the conical pin 3 of a second part 2 which is connected with a shaft 4 via a cylindrical rod. Between cone 3 and shaft 4, the rod carries a thread 6 onto which is screwed a nut 7' of conventional form. In the illustrated position, which corresponds to the implanted state, this nut is at a noticeable distance from the first part 1 of the implant. As can be seen, the parts provided with coinciding reference numerals essentially correspond to those shown in FIG. 1.

In the space between cone 3 and nut 7', the rod is provided with an implant section provided with planar work faces for a holding tool. One planar work face, 8, is visible in FIG. 4. As can be seen in the sectional view along line V—V of FIG. 5, the work face 8 is one of four work faces forming a square and includes a work face 9 disposed parallel to and opposite work face 8. A wrench 10 is shown engaging the other two work faces so as to secure the second part 2 against rotation about its longitudinal axis 11 and simultaneously constitutes a spacer between nut 7' and joint ball 1.

If now the first part 1 is to be released from the second part 2, nut 7', is screwed, by a suitable wrench, in the direction toward cone 3, initially until it comes into contact with wrench 10. If nut 7' is rotated further, wrench 10 is pressed against an abutment face of part 1 and slowly lifts part 1 away from cone 3. During removal of part 1, wrench 10 is moved along axis 11, but remains in engagement with the work faces disposed between thread 6 and cone 3.

According to FIG. 4, wrench 10 has at its underside an opening, or key, which corresponds to the dimensions of the square formed by the work faces 8, 9 at part 2. However, at the upper side of wrench 10, the width of the key is enlarged so that the wrench does not get caught at the base of cone 3 where it projects from part 1.

Nut 7' has a substantially rounded outline which is thus adapted to part 2. As further shown in FIG. 4, nut 7' has an annular projection 12 which, in the implanted state, rests on a projection at shaft 4 so that thread 6 is sealed against penetrating body fluids.

In the detail view of FIG. 6, a longitudinal groove 13 is provided in the implant section between cone 3 and thread 6 in place of work faces 8, 9.

FIG. 7 shows how a grooved nut key can engage in this longitudinal groove instead of a wrench, with the size of the grooved nut key again being selected such that when part 1 is being lifted off, the key bridges the distance between part 1 and nut 7'. Groove 13 extends into cone 3 so that, when part 1 is lifted off cone 3, the groove nut key can move far enough toward the free end of cone 3 without restriction.

It will be understood that the above description of the present invention is susceptible to various modifications, changes and adaptations and the same are intended to be comprehended within the meaning and range of equivalents of the appended claims.

What is claimed is:

1. A bone implant comprising: a first part having a receptacle; a second part having a pin projecting therefrom, said pin having a free end extending away from said second part, said pin having a threaded portion and a conical portion, said conical portion being located between said threaded portion and said free end of said pin and tapering toward said free end of said pin, said conical portion being sized to form a plug-in connection with the receptacle of said first part thereby operatively connecting said first and second parts together; and a nut threadedly engaging said threaded portion, whereby rotation of said nut toward said first part forces said first part away from said second part until said first part is pushed loose from said pin, thereby effectively separating said first part from said second part.

2. Implant as defined in claim 1 wherein one of said first and second parts is provided with surfaces defining work faces for a holding tool so as to transfer a torque against rotation about the thread axis due to movement of said nut.

3. Implant as defined in claim 1 wherein one of said first and second parts comprises an elongated shaft member constructed to be inserted into a bone.

4. Implant as defined in claim 3 constituting a hip joint prosthesis and wherein said second part is a shaft member to be introduced in an intramedullary cavity and said first part is an articular joint element to engage an acetabular portion of a hip joint.

5. Implant as defined in claim 1 wherein said nut is provided with recesses distributed at regular intervals over its circumferential area to serve as elements for transmitting movement forces to said nut from a tool cooperating with said recesses.

6. Implant as defined in claim 5 wherein said recesses are blind bores having round cross sections.

7. Implant as defined in claim 1 wherein said nut has an outer contour shaped to create a transition region merging substantially with the outer contours of said second part and said conical portion of said pin.

8. Implant as defined in claim 1 constituting a joint prosthesis, wherein said first part includes a ball joint which is plugged onto said conical portion, and said nut has an exterior surface composed of a first surface portion configured for engagement with an actuating tool, and a second surface portion adjacent said first part and having a smaller diameter than said first surface portion in order to reduce restriction of the mobility of the associated joint socket.

9. Implant as defined in claim 1 wherein said second part is provided with surfaces defining work faces for a holding tool, disposed between said conical portion and said threaded portion, said work faces being configured and located such that, with a holding tool engaging said work faces, movement of said nut toward said first part causes the holding tool to press against said first part for forcing said first and second parts apart.

10. Implant as defined in claim 9 wherein at least one said work face is planar and is part of a cylinder shaped implant section whose axis extends essentially parallel to the axis of said thread.

11. Implant as defined in claim 5 wherein said recesses are blind bores having polygonal cross sections.

12. Implant as defined in claim 5 wherein said recesses are grooves.

13. Implant as defined in claim 9 wherein at least one said work face is planar and is part of a prism-shaped implant section whose axis extends essentially parallel to the axis of said thread.

14. Implant as defined in claim 3 wherein both of first and second parts are elongated shaft members connectable together for bridging large bone defects.

15. Implant as defined in claim 1 wherein at least one of said first and second parts form a kit comprising a plurality of parts of different lengths and equipped with uniform attachment pieces.

16. Implant as defined in claim 1 wherein said second part further has a shaft fastened to the end of said pin which is remote from said free end of said pin, and said nut is provided with a radially outwardly projecting annular member facing said shaft, and said nut is rotatable for causing said annular member to bear against said shaft so that said annular member and said shaft form a seal which seals said threaded portion against penetration of body fluids from the region surrounding said nut when said implant has been implanted.

17. Implant as defined in claim 9 wherein there are two of said surfaces of said second part which define work faces, and said two surfaces extend parallel to one another.

18. Implant as defined in claim 9, wherein said second part has an outer surface and is provided with a longitudinal groove extending between said conical portion and said threaded portion, and extending to said outer surface, and said longitudinal groove has a side wall which extends to said outer surface and which constitutes one said work face.

* * * * *